United States Patent [19]
Heifetz

[11] Patent Number: 5,015,242
[45] Date of Patent: May 14, 1991

[54] MEDICAL NEEDLE UNIT

[76] Inventor: Milton D. Heifetz, 704 N. Bedford Dr., Beverly Hills, Calif. 90210

[21] Appl. No.: 364,177

[22] Filed: Jun. 12, 1989

[51] Int. Cl.⁵ .............................................. A61M 5/32
[52] U.S. Cl. .................................... 604/198; 604/263
[58] Field of Search ............... 604/198, 192, 263, 110, 604/162, 163, 171

[56] References Cited
U.S. PATENT DOCUMENTS

| | | | |
|---|---|---|---|
| 2,847,995 | 8/1958 | Adams | 604/198 |
| 3,134,380 | 5/1964 | Armao | 604/198 |
| 4,725,267 | 2/1988 | Vaillancourt | 604/198 |
| 4,782,841 | 11/1988 | Lopez | 604/198 |

Primary Examiner—Stephen C. Pellegrino
Attorney, Agent, or Firm—Ilya Zborovsky

[57] ABSTRACT

A medical needle unit has a needle having a tip and insertable in and withdrawable from a patient, and a protective element for preventing accidental puncture by said tip of said needle after the withdrawal of the needle from the body. The protective element is elastic and hood-shaped and also formed so that before the withdrawal of the needle from the body the protective element surrounds the needle and is compressed to assume an accordion shape, and after the withdrawal of the needle from the body the previously compressed protective element automatically expands and covers the tip of the needle.

14 Claims, 2 Drawing Sheets

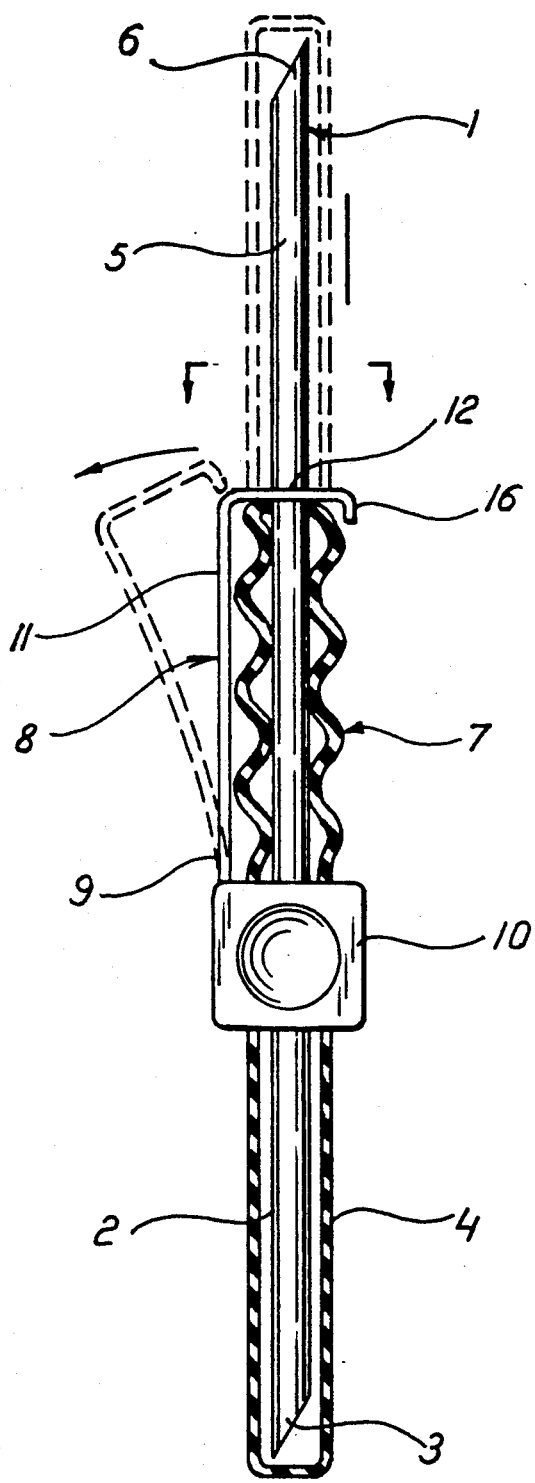
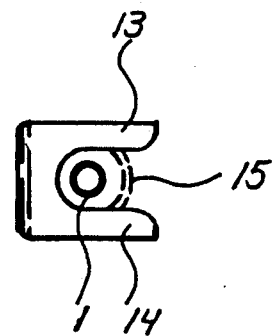
FIG.2
FIG.1

5,015,242

MEDICAL NEEDLE UNIT

BACKGROUND OF THE INVENTION

The present invention relates to medical needle units.

Medical needle units are widely known and used for example for withdrawal of blood or other tissue fluids. After withdrawal of blood or other tissue fluids the needle of the needle unit is withdrawn from a vein, artery or another body area and a tip of the needle is exposed. The needle may be contaminated with diseases, such as for example AIDS HIV- virus or Hepatitis-B virus. A technician, nurse or physician can be accidentally punctured by the exposed needle tip, which in the event of contamination of the needle with the diseases can lead to very serious or even grave consequences. It is to be understood that it is desirable to prevent or at least decrease the tendency of the operator to be accidentally struck by an exposed needle tip.

SUMMARY OF THE INVENTION

Accordingly, it is an object of the present invention to provide a medical needle unit which avoids the disadvantages of the prior art.

More particularly, it is an object of the present invention to provide a medical needle unit which prevents or at least decreases the tendency of the operator to be accidentally struck by an exposed needle tip after withdrawal of the needle from a vein, an artery or another body area.

In keeping with these objects and with others which will become apperent hereinafter, one feature of the present invention resides, briefly stated, in a medical needle unit which is provided with an elastic, hood-shaped protective element formed so that before the withdrawal of a needle from the body the protective element surrounds the needle and is compressed to assume an accordion shape and to expose a tip of the needle, while after the withdrawal of the needle from the body the previously compressed protective element automatically expands and covers the tip of the needle.

When the medical needle unit is designed in accordance with the present invention, it avoids the disadvantages of the prior art and prevents or at least decreases the probability of accidental striking of the operator by the tip of the needle.

In accordance with another feature of the present invention, the inventive medical needle unit can be provided with a retaining element which retains the protective element in its compressed position and can be actuated by the operator to release the protective element and allow its expansion. The retaining element can be bendable out of its engagement with the protective element and provided with a portion which restrains lateral displacement of the protective element.

Still another feature of the present invention is that the protective element can be formed as an initially rectilinear element covering the tip of the needle in its initial position. Then it can be compressed by the operator or due to its abutment against an adjacent region of the body during insertion of the needle to assume its compressed position.

In accordance with a further feature of the present invention, the tip of the protective element can be reinforced for preventing its piercing by the needle tip. The reinforcement can be achieved by increasing the thickness of the protective element in the region of its tip, or by making the tip of the protective element from a different tip-penetration resistant material.

Finally, in accordance with an additional feature of the present invention the protective element in its compressed position can be bent laterally so that the needle extends through its side surface, while the end of the protective element is engaged by the retaining element.

The novel features of the present invention are set forth in particular in the appended claims. The invention itself, however, both as to its construction and its manner of operation will be best understood from the following description of preferred embodiments which is accompanied by the following drawings.

BRIEF DESCRIPTION OF THE DRAWINGS

FIG. 1 is a side view of a medical needle unit in accordance with one embodiment of the present invention;

FIG. 2 is a plan view of the medical needle unit of the embodiment shown in FIG. 1;

DESCRIPTION OF PREFERRED EMBODIMENT

Figure 3:
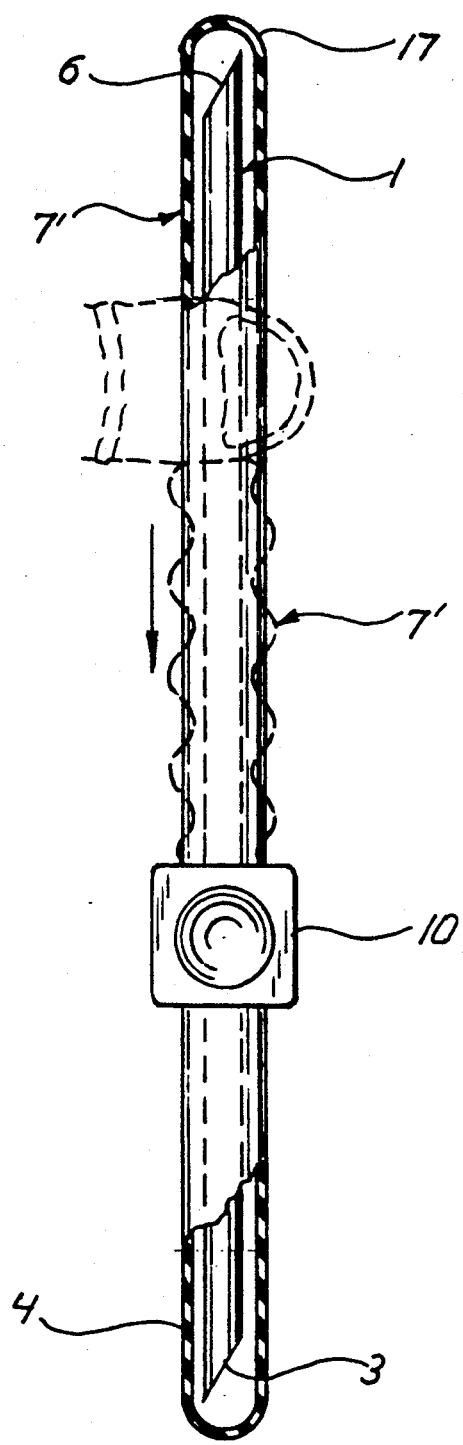
FIG. 3 is a side view of the medical needle unit in accordance with another embodiment of the present invention.

A medical needle unit in accordance with the present invention includes a needle which is identified as a whole with reference numeral 1. The needle 1 has a rear portion 2 which ends in a rear tip 3. The rear portion 2 with the rear tip 3 is surrounded by a sheath 4, for example of rubber. The rear portion 2 of the needle and the sheath 4 cooperate with a not shown container for accumulating blood withdrawn from the patient and with an element for generating suction in the container for withdrawing the blood. This is well known in the art and therefore is not described in detail.

In accordance with the present invention, a front portion 5 of the needle, which has a front tip 6 insertable into the body of the patient, is provided with a protective element. The protective element is identified as a whole with reference numeral 7. The protective element 7 is elastic, for example composed of rubber, and hood-shaped. As can be seen from the drawings, before the withdrawal of the needle from the body and in this embodiment even before the insertion of the needle in the body, the protective element 7 is compressed and assumes an accordion shape, so that the front tip 6 of the needle is exposed. In the compressed position, the protective element is compressed with a prestress, so that it tends to expand.

The protective element 7 is retained in its compressed position shown in solid lines, by a retaining element identified as a whole with reference numeral 8. The retaining element has one end 9 which is immovable relative to the needle. For example, the end 9 is fixedly connected with a hub 10 of the needle. A straight connecting portion 11 of the retaining element extends at one side of the needle substantially parallel to the latter and is bendable. An opposite free end 12 of the retaining element extends transversely to the needle. It is fork-shaped and has two legs 13 and 14 which define therebetween a slot 15 for the needle. A free end of the transverse end or portion 12 of the retaining element is further provided with a downwardly extending restraining portion 16 extending substantially parallel to the connecting portion 11.

In the position shown in FIG. 1 before insertion of the needle tip 6 into the body, the transverse portion 12 retains the protective element 7 in its compressed position, while the restraining portion 16 prevents unauthorized lateral movement of the retaining element and inadvertent release of the protective element. After the insertion of the needle in the body, taking the blood, and before withdrawal of the needle from the body, the operator pushes the retaining element to the left in direction of the arrow so that the retaining element assumes a position shown in broken lines. The upper end of the protective element 7 is released, and the protective element automatically expands under the action of its elastic prestress so as to cover the tip 6 of the needle immediately upon exit from the skin. Thereby the probability of striking the operator by the tip of the needle is eliminated or at least considerably decreased.

The further embodiments of the present invention have some parts which are identical to the part of the first embodiment shown in FIGS. 1 and 2. These parts are identified with the same reference numerals.

The medical needle unit in accordance with a second embodiment shown in FIG. 3 also has a protective element which is identified as a whole with reference numeral 7'. The protective element 7' is formed as an elastic, hood-like element which in its initial position before insertion of the needle 1 in the body is rectilinear. In this position, the upper tip 17 of the protective element 7' surrounds and covers the tip 6 of the needle 1. This position in shown in solid lines. Before insertion of the tip 6 of the needle 1 into the body, the protective element 7' is pulled downwardly by the operator so that the tip 6 of the needle pierces through the protective element and becomes exposed, while the protective element assumes its compressed position in which it has an accordion shape as shown in broken lines.

The protective element can be compressed to assume its accordion shape also in a different manner, during insertion of the needle in the body. During the insertion the upper end of the protective element 7' abuts against the region adjacent to the hole made by the needle, or in other words directly against the body of the patient. It is therefore no longer necessary for the operator to pull the protective element 7' downwardly befor the insertion of the needle into the body. It is to be understood that while in the option with pulling the protective element by the operator the protective element can be composed of a more compression-resistant material, for example of a thicker rubber, in the option with pushing the protective element by the adjacent region of the patient's body the protective element must be composed of a less compression-resistant material, for example of a thinner rubber.

Figure 4:
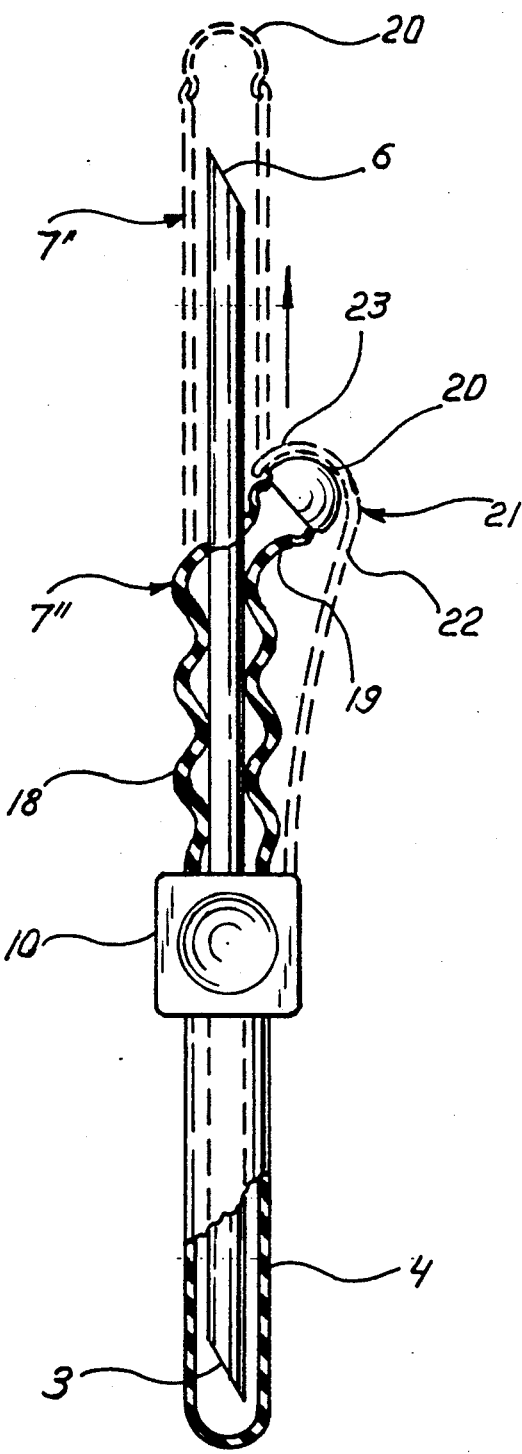
FIG. 4 is a side view of the medical needle unit in accordance with a further embodiment of the present invention.

In the embodiment shown in FIG. 4 the protective element 4" is somewhat bent, so that its one portion 18 extends parallel to the needle, while its another portion 19 is inclined relative to the needle laterally. The needle pierces through the side surface of the protective element, in the initial position of the protective element it is compressed, and a tip 20 of the protective element is retained by a retaining element 21. The retaining element 21 has a first portion 22 fixedly connected with the hub 10 of the needle and bendable, and a second transverse portion 23 engaging the tip 20 of the protective element before actuating of the retaining element by the operator. Before withdrawal of the needle from the body the operator pushes the portion 23 to the right and releases the upper tip of the protective element, so that the latter expands and covers the tip 6 of the needle as the needle exits the skin.

In the embodiment of FIG. 4 the tip 20 is reinforced. In other words, it has an increased piercing-resistance than a remaining portion of the protective element. This measure insures that after the covering of the tip 6 of the needle by the protective element, piercing of the tip of the needle through the tip of the protective element is reliably prevented. The reinforcement of the tip 20 of the protective element can be obtained by making the tip of a material which is different from the material of the remaining portion of the protective element, for example of metal. It can be also obtained by making the tip 20 of the same material and at the same time with a thickness exceeding the thickness of the remaining portion of the protective element (a thicker rubber, or the like). It is to be understood that the reinforced tip can also be provided in the embodiment of FIG. 1.

The present invention is not limited to the details shown since various modifications and structural changes are possible without departing in any way from the spirit of the present invention.

What is desired to be protected by Letters Patent is set forth in particular in the appended claims.

I claim:

1. A medical needle unit, comprising:
   a needle having a tip and insertable in and withdrawable from the body of a patient;
   a protective element for preventing accidental puncture by said tip of said needle after the withdrawal of said needle from the body, said protective element being elastic and hood-shaped and also being formed so that before the withdrawal of said needle from the body said protective element surrounds said needle and is compressed to assume an accordion shape and to expose said tip of said needle, and after the withdrawal of said needle from the body said previously compressed protective element automatically expands and covers said tip of said needle;
   means for retaining said protective element in its compressed position, said retaining means being arranged to cooperate with said protective element and actuatable so as to release the retention of said protective element after the withdrawal of said needle from the body, said retaining means including a retaining element which has one end remote from said tip of said needle and immovable relative to the latter, and another end closer to said tip of said needle and engaging said protective element in its compressed position to retain said protective element in said compressed position.

2. A medical needle unit as defined in claim 1, wherein said retaining element is bendable so that the other end of said retaining element can be moved out of engagement with said protective element by bending said retaining element to thereby release the retention of said protective element after the withdrawal of said needle from the body.

3. A medical needle unit as defined in claim 1, wherein said protective element is formed as an initially rectilinear element which in its initial position covers said tip of said needle and thereafter is compressed so that said tip of said needle pierces through said protective element and becomes exposed while said protective element assumes said accordion shape.

4. A medical needle unit as defined in claim 3, wherein said protective element has such an elasticity that it has to be moved by a user from its rectilinear position to its compressed position before insertion of said tip of said needle in the body.

5. A medical needle unit as defined in claim 1, wherein said protective element has an end portion which before compressing said protective element to assume said accordion shape surrounds and covers said tip of said needle, said end portion being reinforced to prevent accidental penetration of said protective element by said tip of said needle.

6. A medical needle unit as defined in claim 5, wherein said protective element also has a remaining portion, said end portion and said remaining portion of said protective element being composed of a same material, said end portion having a thickness which is greater than a thickness of said remaining portion of said protective element.

7. A medical needle unit as defined in claim 5, wherein said protective element also has a remaining portion, said end portion and said protective element being composed of different materials, said end portion being composed of a material which is more needle tip penetration resistant than said remaining portion of said protective element.

8. A medical needle unit as defined in claim 1, wherein said protective element in its compressed position extends parallel to said needle and has an end section which is engaged by the other end of said retaining element to retain said protective element in said compressed position.

9. A medical needle unit as defined in claim 1, wherein said protective element has a side surface and an end section and arranged so that in its compressed position said protective element is bent laterally so that said needle extends through said side surface of said protective element and said end section extends laterally and is engaged by the other end of said retaining element to retain said protective element in said compressed position.

10. A medical needle unit, comprising:
a needle having a tip and insertable in and withdrawable from the body of a patient;
a protective element for preventing accidental puncture by said tip of said needle after the withdrawal of said needle from the body, said protective element being elastic and hood-shaped and also being formed so that before the withdrawal of said needle from the body said protective element surrounds said needle and is compressed to assume an accordion shape and to expose said tip of said needle, and after the withdrawal of said needle from the body said previously compressed protective element automatically expands and covers said tip of said needle;
means for retaining said protective element in its compressed position, said retaining means being arranged to cooperate with said protective element and actuatable so as to release the retention of said protective element after the withdrawal of said needle from the body, said retaining element having one end connected with said needle and another end freely extending transversely to said needle to extend forwardly before an end of said protective element in its compressed position.

11. A medical needle unit as defined in claim 10, wherein said other end is fork-shaped and has two legs and a slot therebetween formed so that said needle extends through said slot between said legs of said other end of said retaining element.

12. A medical needle unit as defined in claim 10, wherein said retaining element has a connecting portion extending substantially parallel to said needle and connecting said ends with one another, said connecting portion being bendable so that said other end of said retaining element can be moved out of engagement with said protective element by bending said connecting portion.

13. A medical needle unit as defined in claim 12, wherein said retaining element has means for restraining a displacement of said retaining element in a direction transversely to said needle to prevent an inadvertent release of said protective element.

14. A medical needle unit as defined in claim 13, wherein said other end is formed as a transverse portion having one end located at one side of said needle and connected with said connecting portion, said tranverse portion having also another end located at an opposite side of said needle, said restaining means being formed as a restaining portion extending from the other end of said transverse portion substantially parallel to said needle.

* * * * *